United States Patent [19]

Beverly et al.

[11] Patent Number: 4,742,009
[45] Date of Patent: May 3, 1988

[54] METHOD FOR MONITORING STACK GASES FOR URANIUM ACTIVITY

[75] Inventors: Claude R. Beverly; Harold G. Ernstberger, both of Paducah, Ky.

[73] Assignee: The United States of America as represented by the United States Department of Energy, Washington, D.C.

[21] Appl. No.: 751,420

[22] Filed: Jul. 3, 1985

[51] Int. Cl.$^4$ .......................... G01N 1/18; G01N 1/22; G01N 23/00

[52] U.S. Cl. .......................................... 436/57; 436/44; 436/82; 436/177; 436/181; 422/66; 422/83; 423/258; 423/259; 423/260

[58] Field of Search ...................... 436/44, 57, 82, 177, 436/181; 422/66, 83; 423/258, 259, 260

[56] References Cited

U.S. PATENT DOCUMENTS

| | | | |
|---|---|---|---|
| 2,554,414 | 5/1951 | McCleadon | 436/44 |
| 2,797,983 | 7/1957 | Greenspan et al. | 436/82 |
| 3,590,247 | 6/1971 | Holford | 436/57 |
| 3,979,499 | 9/1976 | Heidt | 423/259 X |
| 3,986,029 | 10/1976 | Koske et al. | 250/336.1 |
| 4,051,227 | 9/1977 | Heidt | 423/259 |
| 4,115,067 | 9/1978 | Lyshkow | 436/44 X |
| 4,239,964 | 12/1980 | Robbins et al. | 250/255 |

Primary Examiner—Barry S. Richman
Assistant Examiner—Lynn M. Kummert
Attorney, Agent, or Firm—Earl L. Larcher; Stephen D. Hamel; Judson R. Hightower

[57] ABSTRACT

A method for monitoring the stack gases of a purge cascade of a gaseous diffusion plant for uranium activity. A sample stream is taken from the stack gases and contacted with a volume of moisture-laden air for converting trace levels of uranium hexafluoride, if any, in the stack gases into particulate uranyl fluoride. A continuous strip of filter paper from a supply roll is passed through this sampling stream to intercept and gather any uranyl fluoride in the sampling stream. This filter paper is then passed by an alpha scintillation counting device where any radioactivity on the filter paper is sensed so as to provide a continuous monitoring of the gas stream for activity indicative of the uranium content in the stack gases.

4 Claims, 1 Drawing Sheet

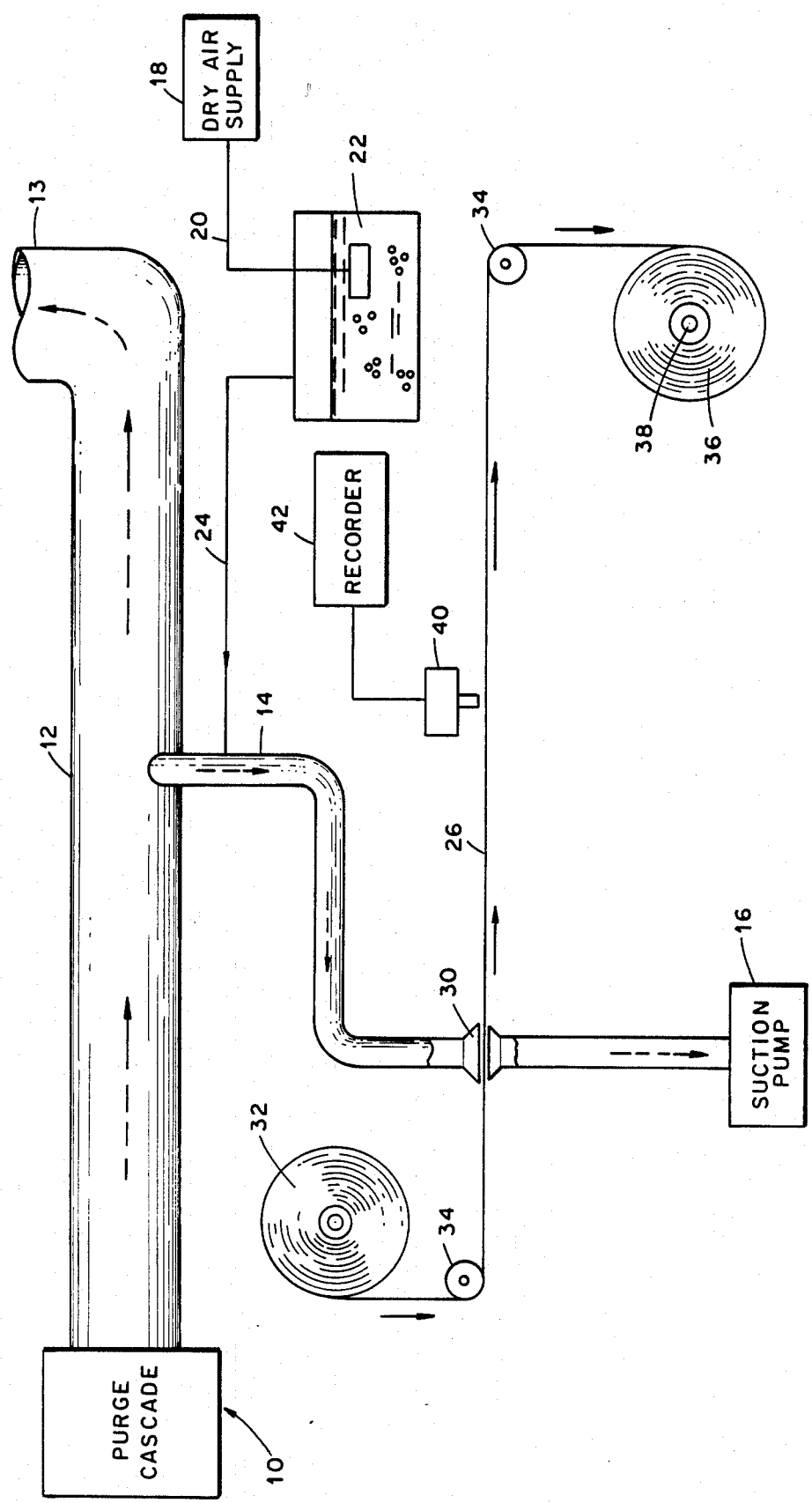

METHOD FOR MONITORING STACK GASES FOR URANIUM ACTIVITY

This invention was made as the result of work under Contract DE-AC05-84OR21400 between Martin Marietta Energy Systems, Inc., and the U.S. Department of Energy.

BACKGROUND OF THE INVENTION

The present invention relates generally to the gaseous diffusion process utilized for the separation of uranium isotopes, and more particularly to a method continually monitoring the stack gases emanating from purge cascades of a gaseous diffusion plant for possible uranium activity.

The enrichment of uranium in the 235 isotope has been achieved for many years in gaseous diffusion systems wherein uranium in a gaseous state, primarily in the form of uranium hexafluoride ($UF_6$), is passed through a series of diffusion barriers to selectively separate the 235 isotope from the 238 isotope until desired enrichment of the uranium in the 235 isotope is achieved. In the gaseous diffusion process one or more purge cascades are used in conjunction with the main enrichment cascade for the purpose of removing nitrogen and other diluents from the uranium hexafluoride stream. These purge cascades differ from the main process cascade due to the separation of the diluents from the uranium hexafluoride and the relative concentration of the isotopic forms of the uranium hexafluoride which remain substantially constant while passing through the purge cascades. In the main cascade the density of the gas remain fairly constant from point to point but in the purge cascade the density varies from that of a mixture having a small amount of nitrogen or other diluent gas in a large amount of uranium hexafluoride at the feed point to a stream of substantially pure diluent gas at the product end. These gases remaining at the product end are routinely discharged into the atmosphere through a stack.

While it is the intent of the purge cascade to remove all of the radioactive material from the gases before they are discharged into the atmosphere some uranium hexafluoride may periodically remain in the stack gases so as to present a possible environmental contamination problem. Previously, the monitoring of the stack gases for radioactive activity was achieved by periodically taking samples of the stack gases at selected locations in the exit lines of the purge cascade. These samples were then transported to an analytical laboratory for determining the uranium content of the stack gases. This somewhat cumbersome procedure presented some problems due to the time lag from taking the sample to determining the presence of radioactive activity in the gases and also presented a considerable potential hazard in that large quantities of radioactive material could escape into the atmosphere between samplings.

SUMMARY OF THE INVENTION

Accordingly, it is the primary aim or objective of the present invention to provide a method wherein the gases emanating from the purge cascade through a stack into the environment may be continually monitored for the presence of uranium activity. This method of sampling the stack gases determines the presence of as well as the extent of uranium activity in the gases in the form of gaseous uranium hexafluoride. The method comprises the steps of contacting a side stream of the stack gases with a stream of air sufficiently saturated with moisture for reacting with and converting the gaseous uranium hexafluoride contacted thereby to particulate uranyl fluoride. This side stream of gases is then contacted with movable filter means such as filter paper which continually intercepts and conveys any particulate uranyl fluoride in the side stream away from the stream of stack gases. The filter means are then continually scanned with radiation sensing means for sensing the presence of and the extent of particulate uranyl fluoride in the side stream of stack gases which is indicative of the presence and extent of uranium hexafluoride in the stack gases.

By converting the gaseous uranium hexafluoride ($UF_6$) to uranyl fluoride ($UO_2F_2$) a solid particulate material is provided so that the radioactive activity therein may be easily monitored by using a simple mechanism such as an alpha scintillation counter. This continuous monitoring of a side stream of the stack gases affords a mechanism by which the purge cascade discharge may be continuously monitored for uranium activity so as to provide a mechanism whereby the presence of uranium activity in the stack gases could trigger an alarm so that a remedy for eliminating the radioactivity from the stack gases can be conducted prior to the occurrence of any detrimental environmental contaminants at a detrimental level.

Other and further objects of the invention will be obvious upon an understanding of the illustrative method about to be described or will be indicated in the appended claims, and various advantages not referred to herein will occur to one skilled in the art upon employment of the invention in practice.

DESCRIPTION OF THE DRAWING

In the drawing, the FIGURE is a schematic representation of a conduit conveying gases from a purge cascade of a diffusion cascade to a suitable exhaust stack with piping and other structural arrangements attached to this conduit for taking a sample or side stream of the stack gases from the conduit in order to continually monitor the sample stream for radioactive activity indicative of the uranium content in the stack gases.

A preferred embodiment of the invention has been chosen for the purpose of illustration and description. The preferred embodiment illustrated is not intended to be exhaustive or to limit the invention to the precise form disclosed. It is chosen and described in order to best explain the principles of the invention and their application in practical use to thereby enable others skilled in the art to best utilize the invention in various embodiments and modifications as are best adapted to the particular use contemplated.

DETAILED DESCRIPTION OF THE INVENTION

With reference to the accompanying drawing, the purge cascade generally shown at 10 of a gaseous diffusion system discharges gases through a conduit 12 into a stack 13 for discharge into the atmosphere. At a suitable location within the conduit 12 a sample or side stream of the stack gases is withdrawn through a conduit 14 by using a suitable suction pump arrangement generally shown at 16. This sample stream once it is monitored for the presence of radioactivity as will be described below can be returned to the exhaust gas stack 13 through a suitable conduit arrangement not shown.

Any trace significant concentration of radioactive material in the gases discharging from the purge cascade 10 is in the form of gaseous uranium hexafluoride. In accordance with the present invention the gaseous hexafluoride is converted to a solid particulate form so that it may be removed from the gaseous stream and monitored for uranium activity. The gas in the side stream in the conduit 14 is contacted with stream of moisture-laden air with the water therein reacting with the gaseous uranium hexafluoride to produce a solid particulate compound, namely, uranium uranyl fluoride according to the reaction:

$$2H_2O + UF_6 \rightarrow UFO_2 + 4HF$$

The stream of moisture-laden air may be readily provided by conveying air from a suitable air supply 18 via conduit 20 into a chamber 22 containing a volume of water so as to provide a sparging arrangement to saturate the air with water. This moisture-laden air is then conveyed from the chamber 22 by conduit 24 to the interior of conduit 14. The air in conduit 24 is sufficiently saturated with water so that there is adequate water to react with any trace levels of the uranium hexafluoride in the side stream in conduit 14 contacted by the moisture-laden air to form the solid uranyl fluoride. The side stream of gases in the conduit 14 containing the moisture-laden air and uranyl fluoride, if any, is then conveyed past a collection point where the particulate material in the sampling stream is intercepted, collected and removed from the conduit 14. The collected material is analytically measured for uranium activity which is indicative of the content of uranium hexafluoride in the stack gases being discharged through stack 13.

In order to intercept, collect and remove the newly formed uranyl fluoride from the conduit 14 a suitable filter mechanism, such as filter paper, which is sufficiently porous to provide for the passage of the gases and yet is capable of intercepting and collecting the particulate uranyl fluoride borne by the gases. This filter paper 26 passed through the full cross section of the conduit 14 through suitable sampling head 30 for intercepting and collecting the solid particulate material in the sampling stream. The filter paper 26 is in the form of a roll 32 which provides an elongated strip of filter paper that can be stripped from roll 32 and continually passed through the sampling head 30 by a suitable pulley arrangement 34 to takeup roll 36 through a drive pulley arrangement 38. As the filter paper 26 passes through the sampling head 30 the solid uranyl fluoride impinges upon the filter paper 26 and is conveyed to the takeup roll 36. During this conveyance the filter paper 26 containing the particulate uranyl fluoride, if any, is continually monitored by an alpha scintillation counter 40. A suitable recording mechanism 42 which may include an alarm system is attached to the alpha counter 40 for providing a readout indicative of the activity measured on the filter paper 26 as it passes by the alpha counter 40. By continuously passing the filter paper 26 through the sampling stream the activity of the stack gases is continuously monitored so that an accurate measurement of the uranium concentration, if any, in the exhaust line of the purge cascade can be constantly monitored for assuring minimum environmental contamination.

It will be seen that the present invention provides a marked improvement over the previously utilized techniques for monitoring radioactivity in stack gases emanating from purge cascade in the gaseous diffusion system. Further, the present invention provides for the relatively economical and highly reliable mechanism for continually analyzing the stack gases.

We claim:

1. A method for sampling stack gases emanating from the purge cascade of a gaseous diffusion cascade system utilized to enrich uranium for determining the presence and extent of uranium in the stack gases in the form of gaseous uranium hexafluoride, comprising the steps of removing a side stream of gases from the stack gases, contacting the side stream of the stack gases with a stream of air sufficiently saturated with moisture for reacting with and converting any gaseous uranium hexafluoride contacted thereby in said side stream of stack gases to particulate uranyl fluoride, thereafter contacting said side stream of stack gases containing said particulate uranyl fluoride with moving filter means for continuously intercepting and conveying the intercepted particulate uranyl fluoride away from said side stream of stack gases, and continually scanning the moving filter means with radiation monitoring means for sensing the presence and extent of particulate uranyl fluoride on the moving filter means which is indicative of the extent of particulate uranyl fluoride in the side stream of stack gases which in turn is indicative of the presence and extent of uranium hexafluoride in the stack gases.

2. The method claimed in claim 1, wherein the moving filter means comprises an elongated strip of filter paper of sufficient porosity to permit the passage of gases therethrough while intercepting particulate material borne by the gases.

3. The method claimed in claim 2, wherein the strip of filter paper is formed into a roll, and wherein the filter paper is continually stripped from the roll, passed through the side stream of gases, scanned, and then rewound in the form of a roll on a take up roll.

4. The method claimed in claim 3, wherein the step of scanning the moving filter paper with the radiation monitoring means is provided by an alpha scintillating counter disposed to scan the filter paper after the passage thereof through the side stream of gases.

* * * * *